United States Patent [19]

Johnston et al.

[11] 4,191,759
[45] Mar. 4, 1980

[54] N-SUBSTITUTED-17β-CARBAMOYLAND-ROST-4-EN-3-ONE 5α REDUCTASE INHIBITORS

[75] Inventors: David B. R. Johnston, Warren, N.J.; Glen E. Arth, deceased, late of Cranford, N.J., by Rose B. Arth

[73] Assignee: Merck & Co., Inc., Rahway, N.J.

[21] Appl. No.: 896,119

[22] Filed: Apr. 13, 1978

[51] Int. Cl.² .......................... A61K 31/56; C07J 9/00
[52] U.S. Cl. .................................. 424/242; 260/397.1; 260/239.5
[58] Field of Search ....................... 424/242; 260/397.1, 260/239.5, 239.55 R

[56] References Cited

U.S. PATENT DOCUMENTS

| 3,917,829 | 11/1975 | Voight et al. | 424/242 |
| 4,088,760 | 5/1978 | Benson et al. | 424/242 |

OTHER PUBLICATIONS

Barber et al., "J. Org. Chem.", 19, (1954) pp. 1758–1765.

Primary Examiner—Elbert L. Roberts
Attorney, Agent, or Firm—Raymond M. Speer; Mario A. Monaco

[57] ABSTRACT

Amides of 17β-carboxy-4-androsten-3-one having the formula:

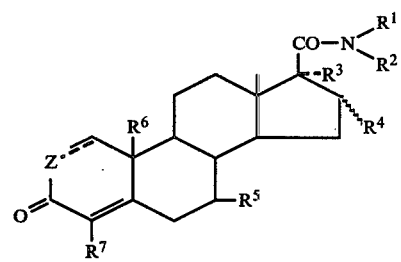

where $R^1$ and $R^2$ are hydrogen (only one may be hydrogen), $C_{1-4}$ alkyl, cyclo $C_{5-6}$ alkyl, phenyl, or together with the nitrogen are a 5 or 6 membered heterocycle with up to one other heteroatom selected from oxygen and nitrogen; $R^3$, $R^4$, $R^5$, and $R^6$ are hydrogen or $C_{1-3}$ alkyl; $R^7$ is hydrogen or cyano; Z is oxygen, N-$R^8$ where $R^8$ is $C_{1-3}$ alkyl, or CH—$R^9$ where $R^9$ is hydrogen, α-fluoro, or α-$C_{1-3}$ alkyl, active as testosterone 5α-reductase inhibitors, and thus useful topically for treatment of acne, seborrhea, female hirsutism and male pattern baldness.

11 Claims, No Drawings

N-SUBSTITUTED-17β-CARBAMOYLANDROST-4-EN-3-ONE 5α REDUCTASE INHIBITORS

BACKGROUND OF THE INVENTION

1. Field of the Invention

The present invention is concerned with novel N-substituted-17β-carbamoylandrost-4-en-3-ones and their use as testosterone 5α-reductase inhibitors.

2. Description of the Prior Art

It is well known in the art that certain undesirable physiological manifestations, such as acne vulgaris, seborrhea, female hirsuitism, and male pattern baldness, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Nonsteroidal antiandrogens have also been developed, for example, 4′-nitro-3′-trifluoromethylisobutyranilide. See Neri et al., Endo., Vol. 91, No. 2 (1972). However, these products, though devoid of hormonal effects, are systemically active, competing with the natural androgens for receptor sites, and hence have a tendency to feminize a male host or the male fetus of a female host.

It more recently became known in the art that the principal mediator of androgenic activity in a target organ is 5α-dihydrotestosterone, a far more potent androgen than testosterone itself, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfeh et al., Steroids, 14, 269 (1969) demonstrated in vitro that methyl 4-androsten-3-one-17β-carboxylate was a testosterone-5α-reductase inhibitor. Then Voight and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotestosterone caused enlargement of the female hamster flank organ, an androgen dependent sebaceous structure. However, concomitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

Attempts by applicants herein to confirm the findings of Voigt and Hsia have failed to demonstrate the same degree of antiandrogenic activity in the female flank organ protocol. Furthermore, the acid and ester of Voigt and Hsia have been shown by applicants to be ineffective in atrophying the male hamster flank organ. This test is a greater challenge for an antiandrogen in that the male flank organ is constantly being stimulated by endogenous testosterone and, therefore, 5α-dihydrotestosterone if the 5α-reductase system is operative.

Surprisingly, it has now been found that the novel compounds of this invention are potent inhibitors of testosterone-5α-reductase in vitro and that N,N-diethyl-17β-carbamoylandrost-4-en-3-one applied topically will significantly atrophy the male hamster flank organ.

It has further been demonstrated that N,N-diethyl-17β-carbamoylandrost-4-en-3-one at relatively high doses does not cause feminization of male fetuses whereas the non-steroidal antiandrogen, 4′-nitro-3′-trifluoromethylisobutyranilide, mentioned previously does cause feminization as determined by the anogenital distance in fetal rate.

In addition to the free acid and ester described above, the unsubstituted amide, 4-androsten-3-one-17β-carboxamide is also a known compound, described in J. Org. Chem., 19, 1758 (1954). However, this compound is quite toxic on subcutaneous administration, whereas the compounds of the present invention have failed to demonstrate any signs of toxicity.

The novel compounds of the present invention are, therefore, potent antiandrogens by virtue of their ability to specifically inhibit testosterone-5α-reductase.

SUMMARY OF THE INVENTION

The present invention is concerned with novel antiandrogenic N-substituted-17β-carbamoylandrost-4-en-3-ones, certain isosteres and derivatives thereof, processes for their preparation, pharmaceutical formulations comprising the novel compounds as active ingredient, and methods of inhibiting 5α-reductase and of treating hyperandrogenic conditions with the novel compounds or their pharmaceutical formulations.

The present invention is particularly concerned with novel compounds of the formula:

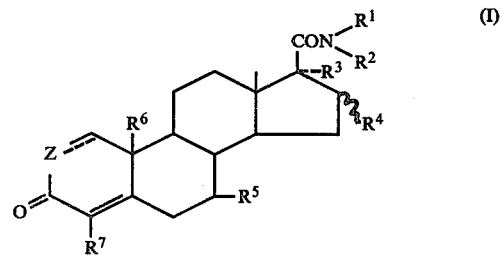

wherein $R^1$ and $R^2$ are the same or different and each represents:
  (1) hydrogen, provided that only one of $R^1$ and $R^2$ may be hydrogen;
  (2) lower alkyl, especially $C_{1-4}$ alkyl, either straight or branched chain such as methyl, ethyl, normal- or iso-propyl, or normal-, secondary-, or tertiary butyl;
  (3) lower cycloalkyl, especially $C_{5-6}$ cycloalkyl, such as cyclopentyl, or cyclohexyl;
  (4) phenyl; or $R^1$ and $R^2$ taken together with the nitrogen to which they are attached represents a 5–6 membered saturated ring comprising up to one other heteroatom selected from oxygen and nitrogen, such as morpholine or piperidine;

$R^3$, $R^4$, $R^5$, $R^6$ represents
  (1) hydrogen; or
  (2) lower alkyl, especially $C_{1-3}$ alkyl, such as methyl, ethyl, normal- or iso-propyl;

$R^7$ represents
  (1) hydrogen; or
  (2) cyano;
Z represents
  (1) O;
  (2) $R^8$-N, wherein $R^8$ is lower alkyl, especially $C_{1-3}$ alkyl such as methyl, ethyl, normal- or iso-propyl; or
  (3) CH—$R^9$, wherein $R^9$ is
    (a) hydrogen,
    (b) α-fluoro, or
    (c) α-lower alkyl, especially $C_{1-3}$ alkyl;

and the dotted line between positions 1 and 2 represents the possibility of a single bond when Z is CH—$R^9$ and a double bond when Z is C—$R^9$.

A preferred embodiment of the novel compounds is that with structural formula:

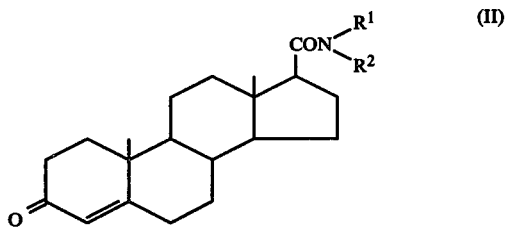

wherein $R^1$ and $R^2$ are as previously defined.

A still more preferred embodiment of the novel compound is that wherein $R^1$ and $R^2$ are $C_{1-4}$ alkyl.

The novel compounds of this invention are prepared by the process of treating the corresponding carboxylic acid chlorides with approximately two molar equivalents of an appropriate secondary amine in an inert organic solvent at 0–15° C. with stirring. The organic solvent is preferably a cyclic ether such as tetrahydrofuran, but the reaction may also be conducted in any other suitable solvent. This reaction may be illustrated as follows:

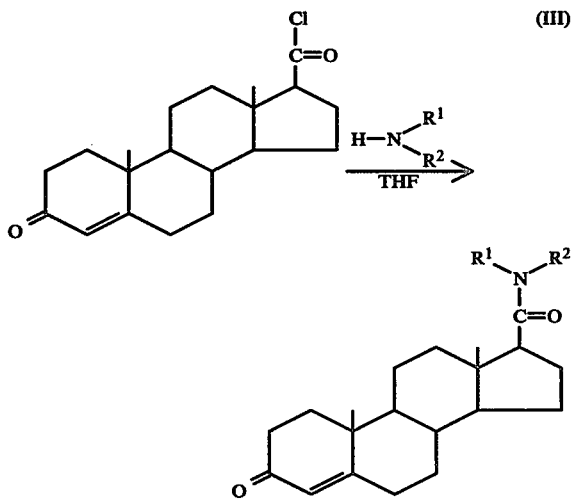

The acid chloride starting material may be prepared by the method of Wilds and Shunk, J. Am. Chem. Soc., 70, 2427 (1948). The starting material, in turn, for the method of Wilds and Shunk, is 3-keto-$\Delta^4$-etiocholenic acid, an available material.

The compounds of the present invention, prepared in accordance with the method described above, are, as already described, potent antiandrogens by virtue of their ability to specifically inhibit testosterone-5α-reductase.

Accordingly, the present invention is particularly concerned with providing a method of treating the hyperandrogenic conditions of acne vulgaris, seborrhea, male pattern baldness and femal hirsuitism by topical administration of the novel compounds of the present invention.

The present invention is thus also concerned with providing suitable topical pharmaceutical formulations for use in the novel methods of treatment of the present invention.

For the treatment of acne vulgaris, seborrhea, female hirsutism and male pattern baldness, the compounds of the present invention are administered in the form of pharmaceutical compositions comprising the active compound in combination with a pharmacologically acceptable carrier adapted for topical administration. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The method of preparing the novel compounds of the present invention, already described above in general terms, may be further illustrated by the following examples.

EXAMPLE 1

N,N-diethyl-17β-carbamoylandrost-4-en-3-one

The starting material, 3-keto-$\Delta^4$-etiocholenyl chloride, was prepared by the method of Wilds and Shunk, J. Am. Chem. Soc., 70, 2427. This acid chloride was stored as a solution in dry tetrahydrofuran so that 10 ml. contained 7.4 millimoles of the acid chloride.

To 5 ml. of dry tetrahydrofuran and 1.87 ml. of freshly distilled diethylamine, stirred well at 0° C., was added dropwise but rapidly 12 ml. of a solution of the acid chloride as prepared above. The reaction was allowed to proceed for 15 min. after which it was added to 150 ml. of ice water. A flocculant precipitate formed which was allowed to age for 45 min. before it was separated by filtration. Because of the product tended to be gummy, it was dissolved in ethyl acetate, washed with water, and dried over anhydrous magnesium sulfate with evaporation of the solvent. The residue was dissolved in benzene and adsorbed on 90 g. of silica gel which had been packed in a column with benzene. After elution with benzene, increasing concentrations of ether in benzene (5 to 20%) were sequentially used to elute the column. The product appeared in the 7.5–20% ether benzene eluates and was collected and recrystallized from ether. The following data were developed for the compound: m.p. 130°–132° C., [α]+114.7° (CHCl₃), λmax 241 mμ, $E_{max}$ 16, 700, with elemental analysis, MS, and NMR consistent with the structural assignment.

EXAMPLES 2–16

Using the procedures described above in Example 1, but substituting for the diethylamine equimolar amounts of amines enumerated below, the following N-substituted-17β-carbamoylandrost-4-en-3-ones are prepared:

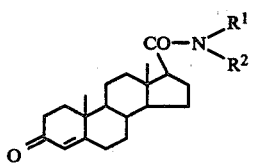

| Exp. No. | amine | $R_1$ | $R_2$ | m.p. (°C.) |
|---|---|---|---|---|
| 2 | $CH_3NHCH_3$ | $CH_3$ | $CH_3$ | 186–188 |
| 3 | $CH_3NHC_2H_5$ | $CH_3$ | $C_2H_5$ | |
| 4 | $CH_3NH$-n-$C_3H_7$ | $CH_3$ | n-$C_3H_7$ | |
| 5 | $C_2H_5NH$-n-$C_3H_7$ | $C_2H_5$ | n-$C_3H_7$ | |
| 6 | i-$C_3H_7NH$-i-$C_3H_7$ | i-$C_3H_7$ | i-$C_3H_7$ | 175–178 |
| 7 | $CH_3NH$-i-$C_3H_7$ | $CH_3$ | i-$C_3H_7$ | |
| 8 | $C_2H_5NH$-i-$C_3H_7$ | $C_2H_5$ | i-$C_3H_7$ | |
| 9 | $CH_3NH$-n-$C_4H_9$ | $CH_3$ | n-$C_4H_9$ | |
| 10 | $C_2H_5NH$-s-$C_4H_9$ | $C_2H_5$ | s-$C_4H_9$ | |
| 11 | n-$C_3H_7NH$-t-$C_4H_9$ | n-$C_3H_7$ | t-$C_4H_9$ | |
| 12 | $C_2H_5NH_2$ | $C_2H_5$ | H | 174–176 |
| 13 | cyclohexyl-NH-cyclohexyl | cyclohexyl | cyclohexyl | 235.5–239.5 |
| 14 | phenyl-N(H)-CH3 | phenyl | $CH_3$ | |

$R^1$ and $R^2$ together with N:

| 15 | piperidine (NH) | piperidine (N) | 209–212 |
| 16 | morpholine (NH) | morpholine (N) | 258–262 |

EXAMPLE 17

Formulations for topical administration of the compounds of the present invention may be prepared in known manner from the following ingredients:

A. Gel Formulation
0.1 mg. disodium edtate
1.30 mg. purified water
300 mg. isopropanol
26 mg. hydroxypropylcellulose
50 mg. N,N-diethyl-17β-carbamoylandrost-4-en-3-one
q.s.a.d. 1 gm. propylene glycol B. Ointment Formulation
50 mg. wool alcohols
150 mg. amichol C
350 mg. white wax
50 mg. N,N-diethyl-17β-carbamoylandrost-4-en-3-one
q.s.a.d. 1 gm. isopropyl myristate

What is claimed is:

1. A compound of the formula:

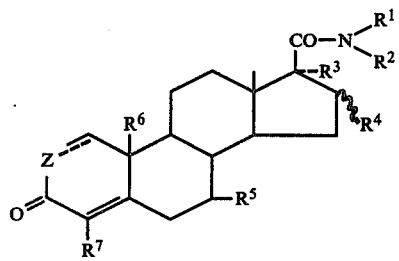

wherein
$R^1$ and $R^2$ are the same or different and each represents:
(1) hydrogen, provided that only one of $R^1$ and $R^2$ may be hydrogen (2) lower alkyl, (3) lower cycloalkyl, (4) phenyl, or
$R^1$ and $R^2$ taken together with the nitrogen to which they are attached represents a 5–6 membered saturated ring comprising up to one other heteroatom selected from oxygen and nitrogen;
$R^3$, $R^4$, $R^5$, and $R^6$ are the same or different and each represents:
(1) hydrogen, or (2) lower alkyl;
$R^7$ represents:
(1) hydrogen or (2) cyano;
Z represents:
$CH$—$R^9$
where $R^9$ is (a) hydrogen, (b) α-fluoro, or (c) α-lower alkyl;
and the dotted line between positions 1 and 2 represents the possibility of a single bond when Z is CH—$R^9$ and a double bond when Z is C—$R^9$.

2. A compound of claim 1 of the formula:

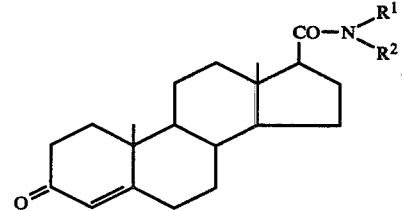

where $R^1$ and $R^2$ are as previously defined.

3. A compound of claim 2 wherein $R^1$ and $R^2$ are lower alkyl.

4. A compound of claim 2 wherein the compound is N,N-diethyl-17β-carbamoylandrost-4-en-3-one.

5. A method of treating the hyperandrogenic conditions of acne vulgaris, seborrhea, male pattern baldness and female hirsuitism comprising topical administration to a patient in need of such treatment of a therapeutically effective amount of a compound of the formula:

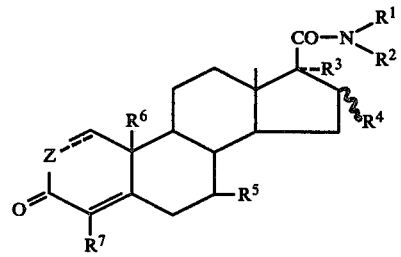

wherein
- $R^1$ and $R^2$ are the same or different and each represents: (1) hydrogen, provided that only one of $R^1$ and $R^2$ may be hydrogen, (2) lower alkyl, (3) lower cycloalkyl, (4) phenyl, or
- $R^1$ and $R^2$ taken together with the nitrogen to which they are attached represents a 5–6 membered saturated ring comprising up to one other heteroatom selected from oxygen and nitrogen;
- $R^3$, $R^4$, $R^5$, and $R^6$ are the same or different and each represents: (1) hydrogen, or (2) lower alkyl;
- $R^7$ represents: (1) hydrogen or (2) cyano;
- Z represents: CH—$R^9$,
  where $R^9$ is (a) hydrogen, (b) α-fluoro, or (c) α-lower alkyl;

and the dotted line between positions 1 and 2 represents the possibility of a single bond when Z is CH—$R^9$ and a double bond when Z is C—$R^9$.

6. The method of claim 5 wherein there is employed a compound of formula:

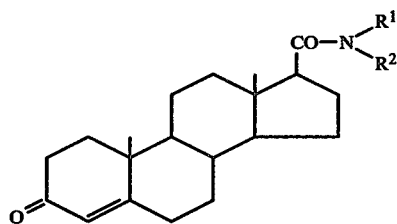

7. The method of claim 5 wherein there is employed N,N-diethyl-17β-carbamoylandrost-4-en-3-one.

8. A method of inhibiting testosterone-5α-reductase in a patient in need of such inhibiting treatment, comprising administration to such a patient of a therapeutically effective amount of a compound of the formula:

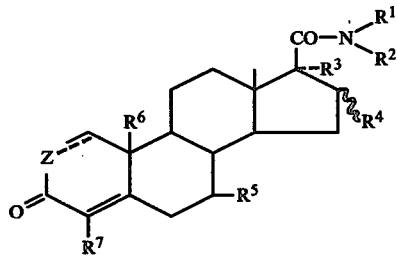

wherein
- $R^1$ and $R^2$ are the same or different and each represents: (1) hydrogen, provided that only one of $R^1$ and $R^2$ may be hydrogen, (2) lower alkyl, (3) lower cycloalkyl, (4) phenyl or
- $R^1$ and $R^2$ taken together with the nitrogen to which they are attached represents a 5–6 membered saturated ring comprising up to one other heteroatom selected from oxygen and nitrogen;
- $R^3$, $R^4$, $R^5$, and $R^6$ are the same or different and each represents: (1) hydrogen, or (2) lower alkyl;
- $R^7$ represents: (1) hydrogen or (2) cyano;
- Z represents: CH—$R^9$,
  where $R^9$ is (a) hydrogen, (b) α-fluoro, or (c) α-lower alkyl;

and the dotted line between positions 1 and 2 represents the possibility of a single bond when Z is CH—$R^9$ and a double bond when Z is C—$R^9$.

9. A pharmaceutical composition comprising a pharmaceutically acceptable carrier and a compound of the formula:

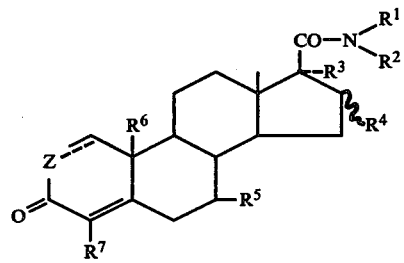

wherein
- $R^1$ and $R^2$ are the same or different and each represents: (1) hydrogen, provided that only one of $R^1$ and $R^2$ may be hydrogen, (2) lower alkyl, (3) lower cycloalkyl, (4) phenyl, or
- $R^1$ and $R^2$ taken together with the nitrogen to which they are attached represents a 5–6 membered saturated ring comprising up to one other heteroatom selected from oxygen and nitrogen;
- $R^3$, $R^4$, $R^5$, and $R^6$ are the same or different and each represents: (1) hydrogen, or (2) lower alkyl;
- $R^7$ represents: (1) hydrogen or (2) cyano;
- Z represents: CH—$R^9$,
  where $R^9$ is (a) hydrogen, (b) α-fluoro, or (c) α-lower alkyl;

and the dotted line between positions 1 and 2 represents the possibility of a single bond when Z is CH—$R^9$ and a double bond when Z is C—$R^9$.

10. The composition of claim 9 wherein there is employed a compound of formula:

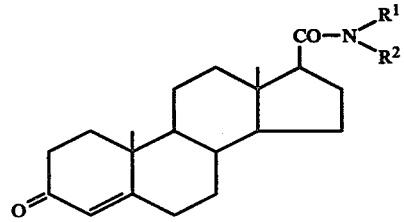

11. The composition of claim 9 wherein there is employed N,N-diethyl-17β-carbamoylandrost-4-en-3-one.